(12) United States Patent
Kim

(10) Patent No.: US 10,083,528 B2
(45) Date of Patent: Sep. 25, 2018

(54) METHOD AND APPARATUS FOR EDITING PARAMETERS FOR CAPTURING MEDICAL IMAGES

(71) Applicant: SAMSUNG ELECTRONICS CO., LTD., Suwon-si (KR)

(72) Inventor: Joo-young Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 45 days.

(21) Appl. No.: 15/275,605

(22) Filed: Sep. 26, 2016

(65) Prior Publication Data

US 2017/0103552 A1 Apr. 13, 2017

(30) Foreign Application Priority Data

Oct. 12, 2015 (KR) .................. 10-2015-0142169

(51) Int. Cl.
*G06T 11/00* (2006.01)
*G06F 3/0484* (2013.01)
*A61B 5/055* (2006.01)
*A61B 6/03* (2006.01)
*A61B 8/08* (2006.01)
(Continued)

(52) U.S. Cl.
CPC ............ *G06T 11/008* (2013.01); *A61B 5/055* (2013.01); *A61B 6/032* (2013.01); *A61B 8/52* (2013.01); *G01R 33/20* (2013.01); *G06F 3/04847* (2013.01); *A61B 5/0002* (2013.01)

(58) Field of Classification Search
CPC ......... G06T 11/008; G01R 33/20; A61B 8/52; A61B 5/055; A61B 6/032; A61B 5/0002; G06F 3/04847
See application file for complete search history.

(56) References Cited

U.S. PATENT DOCUMENTS 8,526,669 B2 * 9/2013 Lavin .................. A61B 8/467
348/239
8,644,336 B2 2/2014 Takada et al.
(Continued)

FOREIGN PATENT DOCUMENTS

JP 2006-231040 A 9/2006
JP 4868862 B2 2/2012

OTHER PUBLICATIONS

Communication dated Sep. 5, 2016 issued by the Korean Intellectual Property Office in counterpart Korean Patent Application No. 10-2015-0142169.
(Continued)

*Primary Examiner* — Ming Hon
(74) *Attorney, Agent, or Firm* — Sughrue Mion, PLLC

(57) ABSTRACT

An apparatus for editing information about a parameter for capturing a medical image includes a storage device configured to store at least one piece of group information including information about a change to the parameter for capturing the medical image and information about an associated parameter to be changed together with the parameter; a display configured to display a parameter change history including the at least one piece of group information; and a controller configured to control the display and the storage device, wherein the at least one piece of group information is arranged based on an order in which a parameter in the at least one piece of group information is changed.

17 Claims, 13 Drawing Sheets

(51) Int. Cl.
*G01R 33/20* (2006.01)
*A61B 5/00* (2006.01)

(56) References Cited

U.S. PATENT DOCUMENTS

| | | | |
|---|---|---|---|
| 8,842,895 B2 | 9/2014 | Sugiura | |
| 2006/0242095 A1* | 10/2006 | Takada | A61B 6/00 706/23 |
| 2007/0091010 A1* | 4/2007 | Richardson | H04N 1/00204 345/2.1 |
| 2007/0094306 A1* | 4/2007 | Kyriazakos | G06Q 10/10 |
| 2010/0046013 A1* | 2/2010 | Bonikowski | B41J 2/0057 358/1.9 |

OTHER PUBLICATIONS

Communication dated Jan. 2, 2017 issued by the Korean Intellectual Property Office in counterpart Korean Patent Application No. 10-2015-0142169.
Communication dated Feb. 13, 2017 issued by the Korean Intellectual Property Office in counterpart Korean Patent Application No. 10-2015-0142169.

* cited by examiner

METHOD AND APPARATUS FOR EDITING PARAMETERS FOR CAPTURING MEDICAL IMAGES

CROSS-REFERENCE TO RELATED APPLICATION

This application claims benefit from Korean Patent Application No. 10-2015-0142169, filed on Oct. 12, 2015, in the Korean Intellectual Property Office, the disclosure of which is incorporated herein in its entirety by reference.

BACKGROUND

1. Field

The present disclosure relates to methods and apparatuses for editing parameters for capturing medical images, and more particularly, to methods and apparatuses for providing a history of editing of parameters for capturing medical images and for editing a parameter by using the history of the editing.

2. Description of Related Art

Medical imaging apparatuses are used to acquire images showing an internal structure of an object. The medical imaging apparatuses are non-invasive examination apparatuses that capture and process images of details of structures, tissue, fluid flow, etc., inside a body and provide the images to a user. A user, e.g., a medical practitioner, may use medical images output from the medical imaging apparatuses to diagnose a patient's condition and diseases.

Examples of medical imaging apparatuses may include a magnetic resonance imaging (MRI) apparatus for providing an MR image, a computed tomography (CT) apparatus, an X-ray apparatus, and an ultrasound diagnosis apparatus.

In detail, among medical imaging apparatuses, an MRI apparatus uses a magnetic field to capture an image of a target object. The MRI apparatus is widely used for the accurate diagnosis of diseases because stereoscopic images of bones, lumbar discs, joints, nerve ligaments, etc. can be obtained at desired angles.

The MRI apparatus uses a radio frequency (RF) multi-coil including a plurality of RF coils, a permanent magnet, gradient coils, etc. to acquire MR signals, and reconstructs an MR image by sampling the acquired MR signals.

Furthermore, a CT apparatus is capable of providing a cross-sectional image of an object and may represent an internal structure (e.g., organs such as a kidney, a lung, etc.) of the object without superimposition of adjacent structures, as compared to a general X-ray apparatus. Due to these advantages, a CT apparatus is widely used for precise diagnosis of diseases.

A CT apparatus emits X-rays towards an object, detects X-rays that have passed through the object, and reconstructs an image by using the detected X-rays.

As described above, medical images obtained by various medical imaging apparatuses represent an object in different ways according to the type of a medical imaging apparatus and a scanning method used.

When a medical imaging apparatus scans an object, various conditions needed for scanning may be referred to as 'parameters'. For example, in MRI, parameters for adjusting a contrast of an image, parameters for adjusting a resolution of an image, and parameters for adjusting an imaging sequence are available. Furthermore, these scanning conditions may be adjusted automatically or manually by a user.

In detail, during medical imaging, parameters may be edited according to a user's intention and be used to acquire a desired image. Since interdependency may exist between parameters, additional computations are required for editing parameters due to the interdependency therebetween.

Therefore, it is necessary to provide a method and apparatus for further facilitating modification of a plurality of interdependent parameters.

SUMMARY

Provided are methods and apparatuses for facilitating editing of a plurality of interdependent parameters.

Provided are methods and apparatuses for providing a history of editing of parameters for capturing medical images and for editing a parameter by using the history of the editing.

Additional aspects will be set forth in part in the description which follows and, in part, will be apparent from the description, or may be learned by practice of the presented exemplary embodiments.

According to an aspect of an exemplary embodiment, an apparatus for editing information about a parameter for capturing a medical image includes a storage device configured to store at least one piece of group information including information about a change to the parameter for capturing the medical image and information about an associated parameter to be changed together with the parameter; a display configured to display a parameter change history including the at least one piece of group information; and a controller configured to control the display and the storage device, wherein the at least one piece of group information is arranged based on an order in which a parameter in the at least one piece of group information is changed.

The apparatus may further include a user input device configured to receive, from a user, information about a change to the parameter, wherein the controller may be further configured to change the parameter based on the received information, to change, if the parameter has an associated parameter to be changed together with the parameter, the associated parameter, and to control the storage device to store information about the change to the parameter and the change of the associated parameter as the at least one piece of group information.

The display may be further configured to display the changed parameter in such a manner as to distinguish the changed parameter from the associated parameter.

The display may be further configured to display the parameter and the associated parameter in such a manner as to distinguish the parameter from the associated parameter.

The user input device may be further configured to receive, from the user, a selection of first group information from the at least one piece of group information, the first group information being included in the parameter change history, and to receive information indicating deletion of the first group information, and the controller may be further configured to cancel a change to all parameters in the first group information by deleting the first group information.

The controller may be further configured to control the display to display a notification when information about a change to a parameter included in the first group information is included in a plurality of pieces of group information in the parameter change history.

The user input device may be further configured to receive a selection of one piece of group information from among the plurality of pieces of group information, and the controller may be further configured to cancel a change to a parameter included in the one piece of group information.

The user input device may be further configured to receive, from the user, a selection of the at least one piece of group information in the parameter change history and a selection of an imaging protocol, and the controller may be further configured to change, based on information about a change to a parameter in the at least one piece of group information, a corresponding parameter for the imaging protocol.

According to another aspect of an exemplary embodiment, a method of editing information about a parameter for capturing a medical image includes storing at least one piece of group information including information about a change to the parameter for capturing a medical image and an associated parameter to be changed together with the parameter; and displaying a parameter change history including at least one piece of group information, wherein the at least one piece of group information is arranged based on an order in which a parameter in the at least one piece of group information is changed.

The storing of the information about the change to the parameter may include receiving, from a user, the information about the change to the parameter; changing the parameter based on the received information; and changing, if the parameter has an associated parameter to be changed together with the parameter, the associated parameter.

The changing of the parameter based on the received information may include displaying the changed parameter in such a manner as to distinguish the changed parameter from the associated parameter.

The displaying of the parameter change history may include displaying the parameter and the associated parameter in such a manner as to distinguish the parameter from the associated parameter.

The method may further include: receiving, from the user, a selection of first group information from the at least one piece of group information, the first group information being included in the parameter change history; receiving, from the user, information indicating deletion of the first group information; and cancelling a change to all parameters in the first group information by deleting the first group information.

The cancelling of the change to all parameters may include displaying a notification when information about a change to a parameter in the first group information is included in a plurality of pieces of group information in the parameter change history.

The displaying of the notification may include: receiving, from the user, information indicating selection of one piece of group information from among the plurality of pieces of group information; and cancelling a change to a parameter included in the one piece of group information.

The method may further include: receiving, from the user, a selection of the at least one piece of group information in the parameter change history; receiving a selection of an imaging protocol from the user; and changing, based on information about a change to a parameter in the at least one piece of group information, a corresponding parameter for the imaging protocol.

According to yet another aspect of an exemplary embodiment, a non-transitory computer-readable recording medium having recorded thereon a program which, when executed, causes a processor to perform the methods described herein.

The parameter may be related to at least one condition used by the apparatus when performing at least one from among emitting radiation toward an object, detecting radiation that has passed through the object, and reconstructing an image using the detected radiation.

The associated parameter may be related to at least one condition used by the apparatus when performing at least one from among emitting radiation toward an object, detecting radiation that has passed through the object, and reconstructing an image using the detected radiation.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
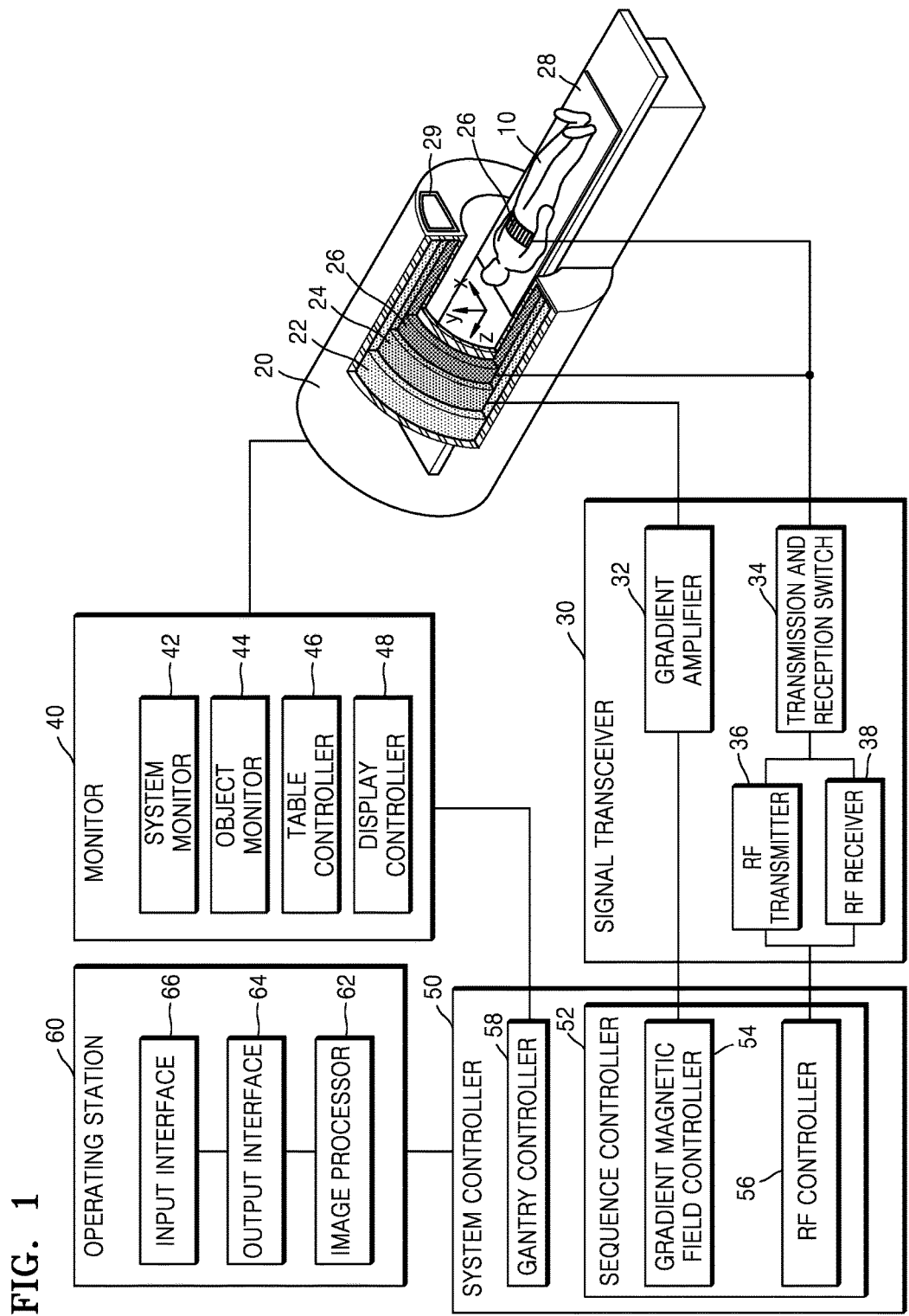
FIG. 1 is a block diagram of a general magnetic resonance imaging (MRI) system.

The attached drawings for illustrating exemplary embodiments of the present disclosure are referred to in order to gain a sufficient understanding of the present disclosure, the merits thereof, and the objectives accomplished by the implementation of the present disclosure. In this regard, the present exemplary embodiments may have different forms and should not be construed as being limited to the descriptions set forth herein. Rather, these exemplary embodiments are provided so that this disclosure will be thorough and complete and will fully convey the concept of the present exemplary embodiments to one of ordinary skill in the art.

Hereinafter, the terms used in the specification will be briefly described, and then the present disclosure will be described in detail.

The terms used in this specification are those general terms currently widely used in the art in consideration of functions regarding the exemplary embodiments, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the exemplary embodiments means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to exemplary embodiments, examples of which are illustrated in the accompanying drawings. In the following description, well-known functions or constructions are not described in detail so as not to obscure the exemplary embodiments with unnecessary detail. Expressions such as "at least one of," when preceding a list of elements, modify the entire list of elements and do not modify the individual elements of the list.

Throughout the specification, an "image" may denote multi-dimensional data composed of discrete image elements (for example, pixels in a two-dimensional image and voxels in a three-dimensional image). For example, the image may be a medical image of an object captured by an X-ray apparatus, a computed tomography (CT) apparatus, a magnetic resonance imaging (MRI) apparatus, an ultrasound diagnosis apparatus, or another medical imaging apparatus.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. The object may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, or a technician who repairs a medical apparatus.

Furthermore, in the present specification, an "MR image" refers to an image of an object obtained by using the nuclear magnetic resonance principle.

Furthermore, in the present specification, a "pulse sequence" refers to continuity of signals repeatedly applied by an MRI apparatus. The pulse sequence may include a time parameter of a radio frequency (RF) pulse, for example, repetition time (TR) or echo time (TE).

Furthermore, in the present specification, a "pulse sequence schematic diagram" shows an order of events that occur in an MRI apparatus. For example, the pulse sequence schematic diagram may be a diagram showing an RF pulse, a gradient magnetic field, an MR signal, or the like according to time.

An MRI system is an apparatus for acquiring a sectional image of a part of an object by expressing, in a contrast comparison, a strength of a MR signal with respect to a radio frequency (RF) signal generated in a magnetic field having a specific strength. For example, if an RF signal that only resonates a specific atomic nucleus (for example, a hydrogen atomic nucleus) is emitted for an instant toward the object placed in a strong magnetic field and then such emission stops, an MR signal is emitted from the specific atomic nucleus, and thus the MRI system may receive the MR signal and acquire an MR image. The MR signal denotes an RF signal emitted from the object. An intensity of the MR signal may be determined according to a density of a predetermined atom (for example, hydrogen) of the object, a relaxation time T1, a relaxation time T2, and a flow of blood or the like.

MRI systems include characteristics different from those of other imaging apparatuses. Unlike imaging apparatuses such as CT apparatuses that acquire images according to a direction of detection hardware, MRI systems may acquire 2D images or 3D volume images that are oriented toward an optional point. MRI systems do not expose objects or examiners to radiation, unlike CT apparatuses, X-ray apparatuses, position emission tomography (PET) apparatuses, and single photon emission CT (SPECT) apparatuses, may acquire images having high soft tissue contrast, and may acquire neurological images, intravascular images, musculoskeletal images, and oncologic images that are required to precisely capturing abnormal tissues.

FIG. 1 is a block diagram of a general MRI system. Referring to FIG. 1, the general MRI system may include a gantry 20, a signal transceiver 30, a monitor 40, a system controller 50, and an operating station 60.

The gantry 20 prevents external emission of electromagnetic waves generated by a main magnet 22, a gradient coil 24, and an RF coil 26. A magnetostatic field and a gradient magnetic field are formed in a bore in the gantry 20, and an RF signal is emitted toward an object 10.

The main magnet 22, the gradient coil 24, and the RF coil 26 may be arranged in a predetermined direction of the gantry 20. The predetermined direction may be a coaxial cylinder direction. The object 10 may be disposed on a table 28 that is capable of being inserted into a cylinder along a horizontal axis of the cylinder.

The main magnet 22 generates a magnetostatic field or a static magnetic field for aligning magnetic dipole moments of atomic nuclei of the object 10 in a constant direction. A precise and accurate MR image of the object 10 may be obtained due to a magnetic field generated by the main magnet 22 being strong and uniform.

The gradient coil 24 includes X, Y, and Z coils for generating gradient magnetic fields in X-, Y-, and Z-axis directions crossing each other at right angles. The gradient coil 24 may provide location information of each region of the object 10 by differently inducing resonance frequencies according to the regions of the object 10.

The RF coil 26 may emit an RF signal toward a patient and receive an MR signal emitted from the patient. In detail, the RF coil 26 may transmit, toward atomic nuclei included in the patient and having precessional motion, an RF signal having the same frequency as that of the precessional motion, stop transmitting the RF signal, and then receive an MR signal emitted from the atomic nuclei included in the patient.

For example, in order to transit an atomic nucleus from a low energy state to a high energy state, the RF coil 26 may generate and apply an electromagnetic wave signal that is an RF signal corresponding to a type of the atomic nucleus, to the object 10. When the electromagnetic wave signal generated by the RF coil 26 is applied to the atomic nucleus, the atomic nucleus may transit from the low energy state to the high energy state. Then, when electromagnetic waves generated by the RF coil 26 disappear, the atomic nucleus to which the electromagnetic waves were applied transits from the high energy state to the low energy state, thereby emitting electromagnetic waves having a Lamor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Lamor frequency. The RF coil 26 may receive electromagnetic wave signals from atomic nuclei included in the object 10.

The RF coil 26 may be realized as one RF transmitting and receiving coil having both a function of generating electromagnetic waves each having an RF that corresponds to a type of an atomic nucleus and a function of receiving electromagnetic waves emitted from an atomic nucleus. Alternatively, the RF coil 26 may be realized as a transmission RF coil having a function of generating electromagnetic waves each having an RF that corresponds to a type of an atomic nucleus, and a reception RF coil having a function of receiving electromagnetic waves emitted from an atomic nucleus.

The RF coil 26 may be fixed to the gantry 20 or may be detachable. When the RF coil 26 is detachable, the RF coil 26 may be an RF coil for a part of the object, such as a head RF coil, a chest RF coil, a leg RF coil, a neck RF coil, a shoulder RF coil, a wrist RF coil, or an ankle RF coil.

The RF coil 26 may communicate with an external apparatus via wires and/or wirelessly, and may also perform dual tune communication according to a communication frequency band.

The RF coil 26 may be a birdcage coil, a surface coil, or a transverse electromagnetic (TEM) coil according to structures.

The RF coil 26 may be a transmission exclusive coil, a reception exclusive coil, or a transmission and reception coil according to methods of transmitting and receiving an RF signal.

The RF coil 26 may be an RF coil having various numbers of channels, such as 16 channels, 32 channels, 72 channels, and 144 channels.

The gantry 20 may further include a display 29 disposed outside the gantry 20 and a display (not shown) disposed inside the gantry 20. The gantry 20 may provide predetermined information to the user or the object 10 through the display 29 and the display respectively disposed outside and inside the gantry 20.

The signal transceiver 30 may control the gradient magnetic field formed inside the gantry 20, i.e., in the bore, according to a predetermined MR sequence, and control transmission and reception of an RF signal and an MR signal.

The signal transceiver 30 may include a gradient amplifier 32, a transmission and reception switch 34, an RF transmitter 36, and an RF receiver 38.

The gradient amplifier 32 drives the gradient coil 24 included in the gantry 20, and may supply a pulse signal for generating a gradient magnetic field to the gradient coil 24 under the control of a gradient magnetic field controller 54. By controlling the pulse signal supplied from the gradient amplifier 32 to the gradient coil 24, gradient magnetic fields in X-, Y-, and Z-axis directions may be synthesized.

The RF transmitter 36 and the RF receiver 38 may drive the RF coil 26. The RF transmitter 36 may supply an RF pulse in a Lamor frequency to the RF coil 26, and the RF receiver 38 may receive an MR signal received by the RF coil 26.

The transmission and reception switch 34 may adjust transmitting and receiving directions of the RF signal and the MR signal. For example, the transmission and reception switch 34 may emit the RF signal toward the object 10 through the RF coil 26 during a transmission mode, and receive the MR signal from the object 10 through the RF coil 26 during a reception mode. The transmission and reception switch 34 may be controlled by a control signal output by an RF controller 56.

The monitor 40 may monitor or control the gantry 20 or devices mounted on the gantry 20. The monitor 40 may include a system monitor 42, an object monitor 44, a table controller 46, and a display controller 48.

The system monitor 42 may monitor and control a state of the magnetostatic field, a state of the gradient magnetic field, a state of the RF signal, a state of the RF coil 26, a state of the table 28, a state of a device measuring body information of the object 10, a power supply state, a state of a thermal exchanger, and a state of a compressor.

The object monitor 44 monitors a state of the object 10. In detail, the object monitor 44 may include a camera for observing a movement or position of the object 10, a respiration measurer for measuring the respiration of the object 10, an electrocardiogram (ECG) measurer for measuring the electrical activity of the object 10, or a temperature measurer for measuring a temperature of the object 10.

The table controller 46 controls a movement of the table 28 where the object 10 is positioned. The table controller 46 may control the movement of the table 28 according to a sequence control of a sequence controller 50. For example, during moving imaging of the object 10, the table controller 46 may continuously or discontinuously move the table 28 according to the sequence control of the sequence controller 50, and thus the object 10 may be photographed in a field of view (FOV) larger than that of the gantry 20.

The display controller 48 controls the display 29 disposed outside the gantry 20 and the display disposed inside the gantry 20. In detail, the display controller 48 may control the display 29 and the display to be on or off, and may control a screen image to be output on the display 29 and the display. Also, when a speaker is located inside or outside the gantry 20, the display controller 48 may control the speaker to be on or off, or may control sound to be output via the speaker.

The system controller 50 may include the sequence controller 52 for controlling a sequence of signals formed in the gantry 20, and a gantry controller 58 for controlling the gantry 20 and the devices mounted on the gantry 20.

The sequence controller 52 may include the gradient magnetic field controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating station 60. Here, the pulse sequence includes all information required to control the gradient amplifier 32, the RF transmitter 36, the RF receiver 38, and the transmission and reception switch 34. For example, the pulse sequence may include information about a strength, an application time, and application timing of a pulse signal applied to the gradient coil 24.

The operating station 60 may request the system controller 50 to transmit pulse sequence information while controlling an overall operation of the MRI system.

The operating station 60 may include an image processor 62 for receiving and processing the MR signal received by the RF receiver 38, an output interface 64, and an input interface 66.

The image processor 62 may process the MR signal received from the RF receiver 38 so as to generate MR image data of the object 10.

The image processor 62 receives the MR signal received by the RF receiver 38 and performs any one of various signal processes, such as amplification, frequency transformation, phase detection, low frequency amplification, and filtering, on the received MR signal.

The image processor 62 may arrange digital data in a k space (for example, also referred to as a Fourier space or a frequency space) of a memory, and rearrange the digital data into image data via 2D or 3D Fourier transformation.

The image processor 62 may perform a composition process or a difference calculation process on the image data if required. The composition process may be an addition process performed on a pixel or a maximum intensity projection (MIP) process performed on a pixel. The image processor 62 may store not only the rearranged image data but also image data on which a composition process or a difference calculation process is performed, in a memory (not shown) or an external server.

The image processor 62 may perform any of the signal processes on the MR signal in parallel. For example, the image processor 62 may perform a signal process on a plurality of MR signals received by a multi-channel RF coil in parallel so as to rearrange the plurality of MR signals into image data.

The output interface 64 may output image data generated or rearranged by the image processor 62 to the user. The output interface 64 may also output information required for the user to manipulate the MRI system, such as a user interface (UI), user information, or object information. The output interface 64 may be a speaker, a printer, a cathode-ray tube (CRT) display, a liquid crystal display (LCD), a plasma display panel (PDP), an organic light-emitting device (OLED) display, a field emission display (FED), a light-emitting diode (LED) display, a vacuum fluorescent display (VFD), a digital light processing (DLP) display, a flat panel display (FPD), a 3-dimensional (3D) display, a transparent display, or any one of other various output devices that are well known to one of ordinary skill in the art.

The user may input object information, parameter information, a scan condition, a pulse sequence, or information about image composition or difference calculation by using the input interface 66. The input interface 66 may be a keyboard, a mouse, a track ball, a voice recognizer, a gesture recognizer, a touch screen, or any one of other various input devices that are well known to one of ordinary skill in the art.

The signal transceiver 30, the monitor 40, the system controller 50, and the operating station 60 are separate components in FIG. 1, but it will be obvious to one of ordinary skill in the art that respective functions of the signal transceiver 30, the monitor 40, the system controller 50, and the operating station 60 may be performed by another component. For example, the image processor 62 converts the MR signal received from the RF receiver 38 into a digital signal in FIG. 1, but alternatively, the conversion of the MR signal into the digital signal may be performed by the RF receiver 38 or the RF coil 26.

The gantry 20, the RF coil 26, the signal transceiver 30, the monitor 40, the system controller 50, and the operating station 60 may be connected to each other by wire or wirelessly, and when they are connected wirelessly, the MRI system may further include an apparatus (not shown) for synchronizing clock signals therebetween. Communication between the gantry 20, the RF coil 26, the signal transceiver 30, the monitor 40, the system controller 50, and the operating station 60 may be performed by using a high-speed digital interface, such as low voltage differential signaling (LVDS), asynchronous serial communication, such as a universal asynchronous receiver transmitter (UART), a low-delay network protocol, such as error synchronous serial communication or a controller area network (CAN), optical communication, or any of other various communication methods that are well known to one of ordinary skill in the art.

Figure 2:
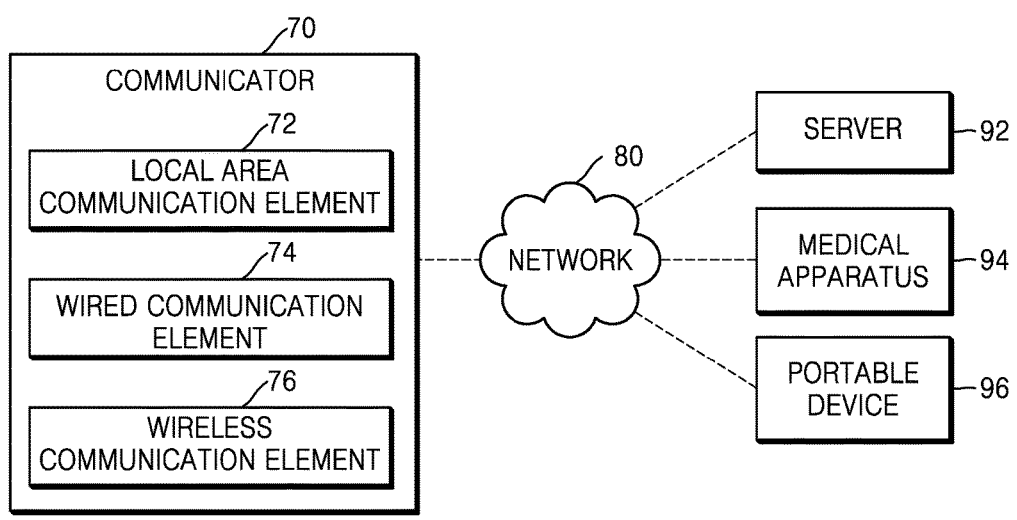
FIG. 2 illustrates a configuration of a communicator according to an exemplary embodiment.

FIG. 2 illustrates a configuration of a communicator 70 according to an exemplary embodiment. Referring to FIG. 2, the communicator 70 may be connected to at least one of the gantry 20, the signal transceiver 30, the monitor 40, the system controller 50, and the operating station 60 described with reference to FIG. 1.

The communicator 70 may transmit or receive data to or from a hospital server or another medical apparatus in a hospital, which is connected through a picture archiving and communication system (PACS), and perform data communication according to the digital imaging and communications in medicine (DICOM) standard.

As shown in FIG. 2, the communicator 70 may be connected to a network 80 by wire or wirelessly to communicate with a server 92, a medical apparatus 94, or a portable device 96.

In detail, the communicator 70 may transmit or receive data related to the diagnosis of an object through the network 80, and may also transmit or receive a medical image captured by the medical apparatus 94, such as a CT apparatus, an MRI apparatus, or an X-ray apparatus. In addition, the communicator 70 may receive a diagnosis history or a treatment schedule of the object from the server 92 and use the same to diagnose the object. The communicator 70 may perform data communication not only with the server 92 or the medical apparatus 94 in a hospital, but also with the portable device 96, such as a mobile phone, a personal digital assistant (PDA), or a laptop of a doctor or patient.

Furthermore, the communicator 70 may transmit information about a malfunction of the MRI system or about quality of a medical image to a user through the network 80, and receive a feedback regarding the information from the user.

The communicator 70 may include at least one component that enables communication with an external device. For example, the communicator 70 may include a local area communication element 72, a wired communication element 74, and a wireless communication element 76.

The local area element module 72 refers to a module for performing local area communication with a device located within a predetermined distance. Examples of local area communication techniques according to various exemplary embodiments may include, but are not limited to, wireless LAN, Wi-Fi, Bluetooth, Zigbee, Wi-Fi Direct (WFD), Ultra wideband (UWB), Infrared Data Association (IrDA), Bluetooth Low Energy (BLE), and Near Field Communication (NFC).

The wired communication element 74 refers to a module for performing communication by using electric signals or optical signals. Examples of wired communication technology according to various exemplary embodiments include wired communication techniques using a pair cable, a coaxial cable, and an optical fiber cable, and other wired communication techniques that are apparent to those of ordinary skill in the art.

The wireless communication element 76 transmits or receives a wireless signal to or from at least one of a base station, an external apparatus, and a server in a mobile communication network. Here, the wireless signal may be a voice call signal, a video call signal, or data in any one of various formats for transmission and reception of a text/multimedia message.

In the MRI system described with reference to FIGS. 1 and 2, various parameters may be adjusted during scanning in order to obtain an MR image by scanning an object. Examples of parameters that are to be adjusted may include number of slices, slice gap, position, orientation, phase encoding direction, phase oversampling, and slice thickness.

Furthermore, the type of parameters may vary according to specifications and/or functions of the MRI system.

As described above, when one of a plurality of parameters having interdependency therebetween is changed to a certain value, values of other parameters that are dependent upon the changed parameter need to be newly calculated and changed. Furthermore, if the values of other parameters that are dependent on the changed parameter are automatically changed), it is necessary to output a user interface (UI) that allows a user to more easily identify the changed parameter and a change history.

A method and apparatus for providing an editing history notifying a change or modification of a plurality of parameters which are dependent upon one another and editing parameters by using the editing history will now be described in detail.

Figure 3:
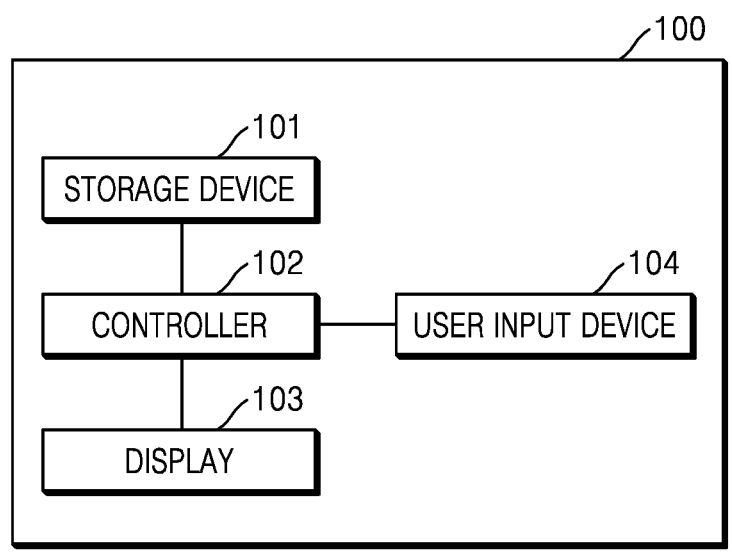
FIG. 3 is a block diagram of an apparatus for editing parameters according to an exemplary embodiment.

FIG. 3 is a block diagram of an apparatus 100 for editing parameters (hereinafter, referred to as a 'parameter editing apparatus') according to an exemplary embodiment. The parameter editing apparatus 100 according to the present exemplary embodiment may be included in the MRI system described with reference to FIGS. 1 and 2. Furthermore, the parameter editing apparatus 100 of FIG. 3 may correspond to at least one of the server 92, the medical apparatus 94, and the portable device 96 described with reference to FIG. 2. Referring to FIG. 3, the parameter editing apparatus 100 may include a storage device 101, a controller 102, a display 103, and a user input device 104.

When the parameter editing apparatus 100 is included in the MRI system described with reference to FIGS. 1 and 2, the controller 102 may correspond to a part or all of the system controller 50 and the monitor 40. The display 103 and the user input device 104 may respectively correspond to the output interface 64 and the input interface 66 described with reference to FIG. 1. Thus, descriptions that are already provided above with reference to FIGS. 1 and 2 will not be repeated below.

The storage device 101 stores information about a change to a parameter for capturing a medical image and its associated parameter that needs to be changed together with the parameter as one piece of group information. In this case, group information may include information about a change to at least one parameter. In detail, the group information may include information about a change to parameters having interdependency therebetween. Information about a change to a parameter may include values of the parameter before and after the change.

The display 103 displays a parameter change history. The parameter change details may include at least one piece of group information. According to an exemplary embodiment, the display 103 may display the parameter change details in a separate window. Furthermore, the display 103 may display a changed parameter and an associated parameter in one piece of group information in such a manner as to distinguish them from each other. According to an exemplary embodiment, the at least one piece of group information included in the parameter change history is arranged based on the order in which parameters in the at least one piece of group information are changed.

The controller 102 controls the storage device 101, the display 103, and the user input device 104. When a parameter is changed, the controller 102 may determine at least one associated parameter that needs to be changed together with the changed parameter. The controller 102 may also determine a variation of the at least one associated parameter based on a variation of the changed parameter. Based on the variation of the determined at least one associated parameter, the controller 102 may change the at least one associated parameter.

The controller 102 may combine information about a change to a parameter and its associated parameter into one group and create one piece of group information. The controller 102 may control the storage device 101 to store the created one piece of group information as a parameter change history. When a parameter change history includes at least one piece of group information, the controller 102 may arrange the at least one piece of group information based on the order that parameters in the at least one piece of group information are changed.

The controller 102 may receive information about a change to a parameter received via the user input device 104. In detail, the user may request a change to a parameter via the user input device 104. Then, the user input device 104 may transmit information corresponding to a user's request for the change to the controller 102. The controller 102 may change the parameter and its associated parameter based on the user input received by the user input device 104.

The controller 102 may control the user input device 104 to receive information indicating selection of first group information included in a parameter change history. The controller 102 may also control the user input device 10 to receive information indicating deletion of the first group information. The controller 102 may cancel a change to all parameters in the first group information by deleting the first group information.

Information about a change to a parameter that is the same as a parameter included in the first group information may also be contained in second group information that is another piece of group information included in a parameter change history. In this case, the controller 102 may provide a notification to the user. According to an exemplary embodiment, the controller 102 may provide a notification to the user via the display 103.

As a way of providing a notification to the user, the controller 102 may provide a user with a message that allows the user to select one of a plurality of groups including the first and second groups. In an exemplary embodiment, the controller 102 may provide the message to the user via the display 103. The controller 102 may control the user input device 104 to receive a user input for selecting one group. The controller 102 may cancel a change to a parameter by deleting the group selected by the user.

According to an exemplary embodiment, the controller 102 may control the user input device 104 to receive a user input for selecting an imaging protocol and third group information included in a parameter change history. The controller 102 may change a parameter in the selected imaging protocol based on information about a change to a parameter included in the third group information. For example, the controller 102 may change a parameter in the selected imaging protocol to be the same as a value to which a parameter included in the third group information is changed.

Figure 4:
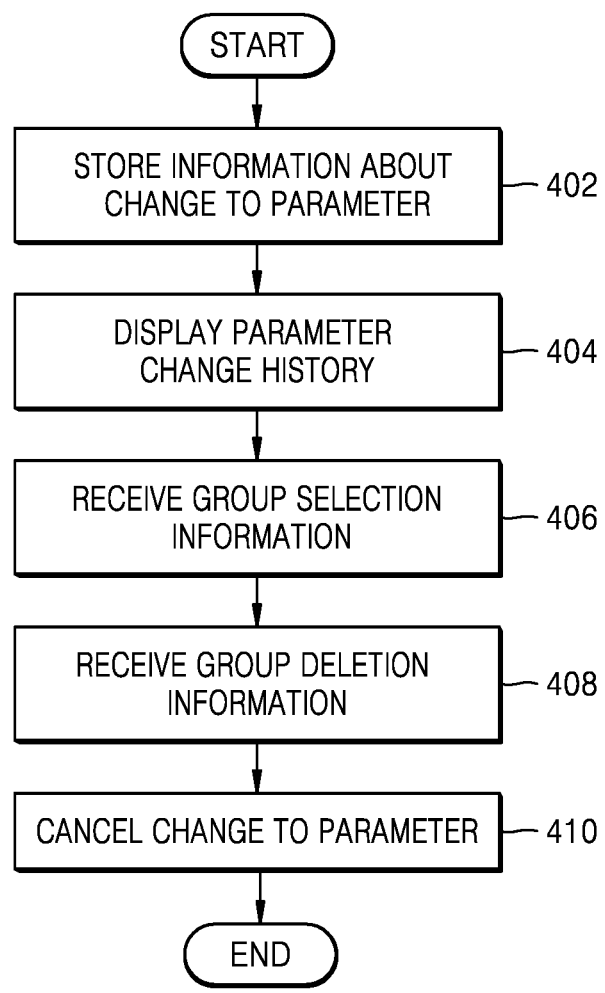
FIG. 4 is a flowchart of a method of editing parameters according to an exemplary embodiment.

FIG. 4 is a flowchart of a method of editing parameters according to an exemplary embodiment. The method may be performed by the parameter editing apparatus 100 described with reference to FIG. 3 and include the same operations as performed by the parameter editing apparatus 100.

An example in which the method is performed by the parameter editing apparatus 100 described with reference to FIG. 3 will now be described in detail. The parameter editing apparatus 100 stores, as one piece of group information, information about a change to a parameter for capturing a medical image and an associated parameter which needs to be changed together with the parameter (operation 402).

According to an exemplary embodiment, the parameter editing apparatus 100 may store, as one piece of group information, information about a change to a parameter changed by the user and its associated parameter which needs to be changed together with the changed parameter. Group information may include information about a change to at least one parameter. Information about a change to a parameter may include a value of the parameter before the change and a value of the parameter after the change.

The parameter editing apparatus 100 displays a parameter change history including at least one piece of group information (operation 404). The parameter change history may include at least one piece of information. According to an exemplary embodiment, the parameter editing apparatus 100 may display the parameter change history in a separate window.

Furthermore, the parameter editing apparatus 100 may display changed parameter and associated parameter in one piece of group information in such a manner as to distinguish them from each other. According to an exemplary embodiment, the at least one piece of group information included in the parameter change history is arranged based on the order that parameters in the at least one piece of group information are changed.

The parameter editing apparatus 100 may receive information indicating selection of first group information included in the parameter change history (operation 406).

The parameter editing apparatus 100 may receive information indicating deletion of the first group information (operation 408). In operations 406 and 408, the information indicating selection of the first group information and the information indicating deletion thereof are not limited to a specific type of information. For example, selection and deletion of the first group information may be performed simultaneously. In this case, the information indicating selection of the first group information and the information indicating deletion thereof may represent the same operation.

Furthermore, 'selection' and 'deletion' may be referred to by other terms. For example, the terms 'determination', 'restoration', 'cancellation', or 'change cancellation' may be used instead of 'selection' and 'deletion', but exemplary embodiments are not limited thereto.

The parameter editing apparatus 100 may cancel a change to all parameters included in the selected first group information by deleting the first group information (operation 410).

Figure 5:
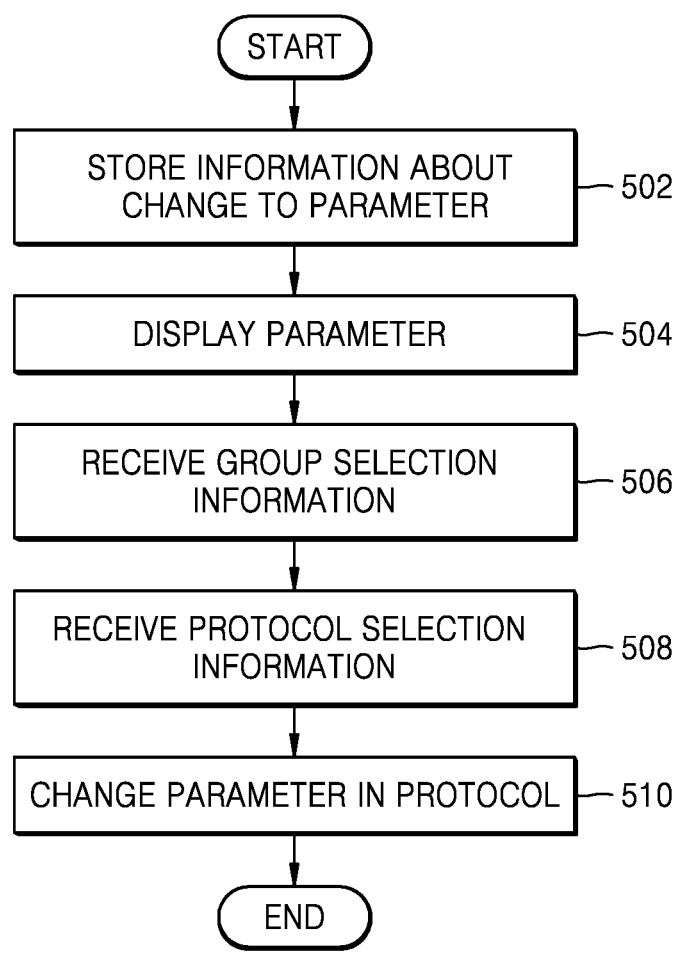
FIG. 5 is a flowchart of a method of editing parameters according to another exemplary embodiment.

FIG. 5 briefly illustrates a method of editing parameters according to an exemplary embodiment. The method of editing parameters illustrated as a flowchart of FIG. 5 is another exemplary embodiment of the method of FIG. 4. Thus, although omitted hereinafter, the descriptions of the method with reference to FIG. 4 may apply to the method of FIG. 5.

The parameter editing apparatus 100 stores, as one piece of group information, information about a change to a parameter for capturing a medical image and an associated parameter which needs to be changed together with the parameter (operation 502).

The parameter editing apparatus 100 displays a parameter change history including at least one piece of group information (operation 504). Operations 502 and 504 may respectively correspond to operations 402 and 404 described with reference to FIG. 4.

The parameter editing apparatus 100 receives, from a user, information indicating selection of first group information included in the parameter change history (operation 506).

The parameter editing apparatus 100 receives information indicating selection of an imaging protocol from the user (operation 508).

The parameter editing apparatus 100 changes a parameter in the imaging protocol based on information about change of a parameter included in the first group information (operation 510).

Figure 6:
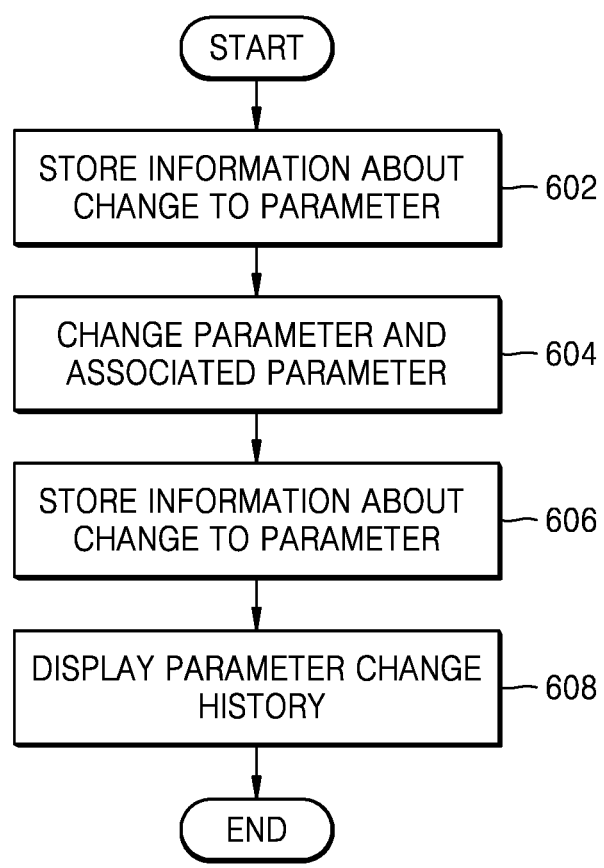
FIG. 6 is a flowchart of a method of editing parameters according to another exemplary embodiment.

FIG. 6 is a flowchart of a method of editing parameters according to another exemplary embodiment. Referring to FIG. 6, the parameter editing apparatus 100 may receive information about change to a parameter from a user (operation 602). For example, the parameter editing apparatus 100 may allow the user to directly enter a value of the parameter or receive an input for increasing or decreasing a value of the parameter by using a button.

The parameter editing apparatus 100 may change the parameter and an associated parameter based on the received information (operation 604).

For example, when the parameter is changed, the parameter editing apparatus 100 may determine at least one associated parameter that needs to be changed together with the changed parameter. The parameter editing apparatus 100 may also determine a variation of the at least one associated parameter based on a variation of the changed parameter. Based on the determined variation of the at least one associated parameter, the controller 102 may change the at least one associated parameter.

Figure 7:
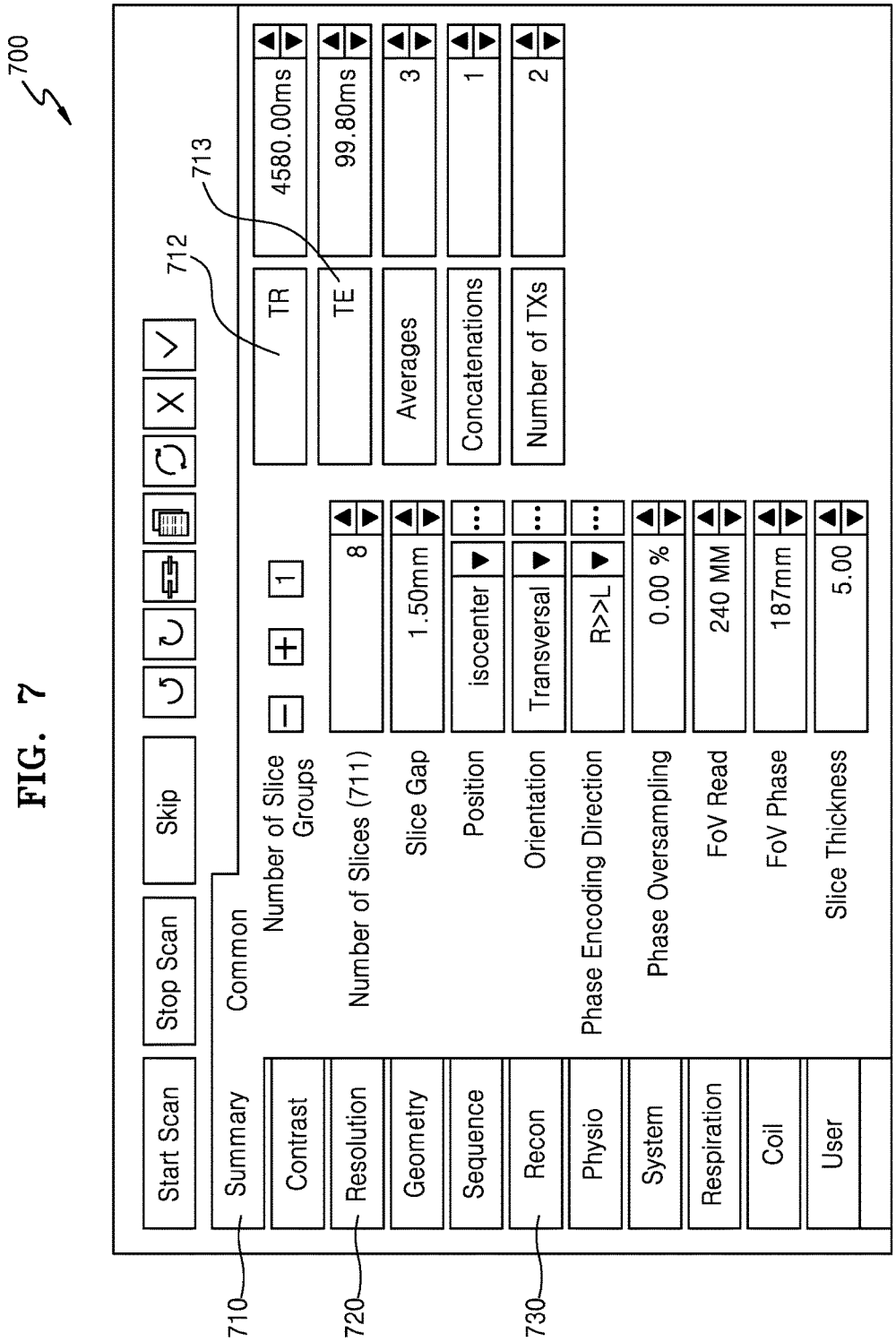
FIG. 7 illustrates an example of a parameter editing screen.

Referring to FIG. 7, parameter 711 is a parameter for setting the number of slices and may be a parameter changed based on a user input. Parameters 712 and 713 may be associated parameters that need to be changed together with the parameter 711. In detail, when the number of slices is adjusted, repetition time (TR) and echo time (TE) need to be adjusted accordingly. Thus, a parameter for adjusting the number of slices and parameters for adjusting TR and TE may be associated with each other. In this case, the storage device 101 may store information about change to the parameter for adjusting the number of slices and the parameters for adjusting TR and TE as one piece of group information.

The parameter editing apparatus 100 may store information about a change to parameters (operation 606). According to an exemplary embodiment, the parameter editing apparatus 100 may store the information about a change to the parameter changed by the user and the associated parameter that needs to be changed together with the changed parameter as one piece of group information. Group information may include information about change to at least one parameter. Information about change to a parameter may include a value of the parameter before change and a new value to which the parameter is changed.

The parameter editing apparatus 100 displays a parameter change history (operation 608). The parameter change history may include at least one piece of group information. According to an exemplary embodiment, the parameter editing apparatus 100 may display the parameter change history in a separate window. Furthermore, the parameter editing apparatus 100 may display changed parameter and associated parameter in one piece of group information in such a manner as to distinguish them from each other. According to an exemplary embodiment, the at least one piece of group information included in the parameter change history is arranged based on the order that parameters in the at least one piece of group information are changed.

Figure 8:
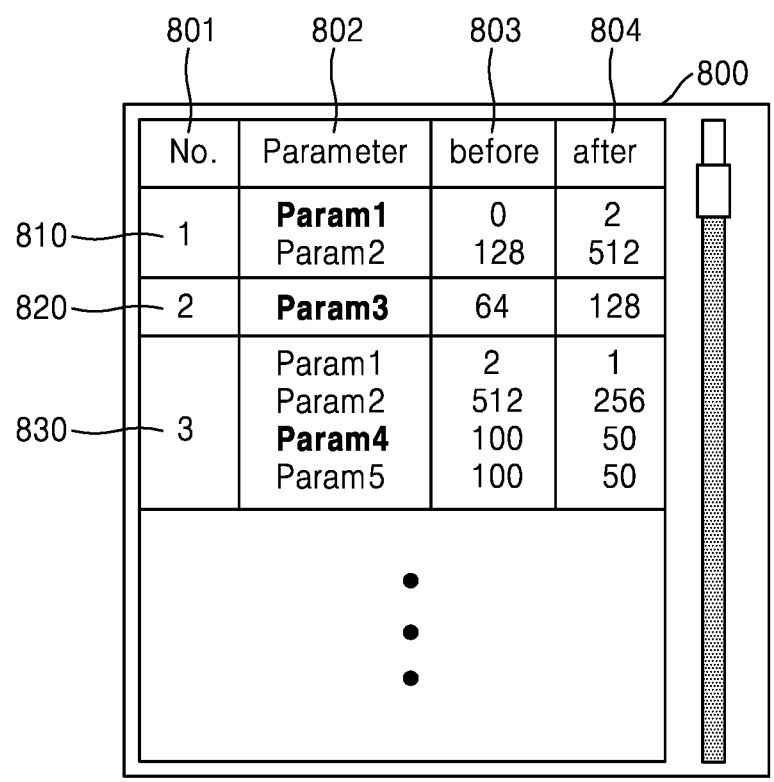
FIG. 8 shows an example of a method of displaying a parameter editing history.

Referring to FIG. 8, the parameter editing apparatus 100 may display a parameter change detail 800 in a separate window. The parameter change history 800 may include at least one group, i.e., group 1 810, group 2 820, and group 3 830. Each of the at least one group 810, 820, and 830 may include at least one parameter.

The parameter change history 800 may include at least one of a group field (No. field 810) identifying each group, a parameter field (Parameter field 802) indicating a parameter included in each group, a before field 803 indicating a value of a parameter before the change, and an after field 804 indicating a value of the parameter after the change.

The parameter editing apparatus 100 may differently display, even in the parameter change history 800, a parameter changed based on a user input and its associated parameter. For example, in order to display a parameter and its associated parameter differently from each other, the parameter editing apparatus 100 may differentiate at least one of a style, a color, a size, a thickness, a background, and an effect of a letter in which the parameter and its associated parameter are displayed. However, the parameter and its associated parameter may be displayed differently in various other ways.

Referring to FIG. 8, the group 1 810 may include two parameters Param1 and Param2. According to an exemplary embodiment, the parameter Param1 may be a parameter changed based on a user input, and the parameter Param2 may be an associated parameter. In an exemplary embodiment, the parameter editing apparatus 100 may display the parameters Param1 and Param2 differently from each other. As shown in FIG. 8, the parameter editing apparatus 100 may display the parameters Param1 and Param2 in bold and normal letters, respectively.

According to an exemplary embodiment, a parameter changed based on a user input may not have an associated parameter. Referring to FIG. 3, the group 2 820 may include only parameter Param3 that is a parameter changed based on a user input. According to another exemplary embodiment, a parameter changed based on a user input may have a plurality of associated parameters. The group 3 830 may include parameter Param4 that is a parameter changed based on a user input and its associated parameters Param1, Param2, and Param5.

According to an exemplary embodiment, the parameter editing apparatus 100 may arrange each piece of group information based on the order in which a parameter in each piece of group information is changed. Referring to FIG. 8, the group 1 810 may be a group including a parameter that has been changed first. Furthermore, the group 3 830 may be a group including a parameter that has been changed last. In another exemplary embodiment, each piece of group information may be arranged in the reverse order.

The parameter editing apparatus 100 may display a user's memo in a parameter editing history. For example, the user may include a memo including a reason for editing each parameter in the parameter editing history. According to an exemplary embodiment, when the user edits a parameter, a window may be displayed which allows the user to enter a reason for editing the parameter.

Referring to FIG. 8, a piece of group information (corresponding to each of the group 1 810, group 2 820, and group 3 830) may include a user's memo. For example, a memo corresponding to the group 1 810 may be included between the group 1 810 and group 2 820. In an exemplary embodiment, when the user clicks on the group 1 810, a memo indicating a reason for editing a parameter may be displayed.

Figure 9:
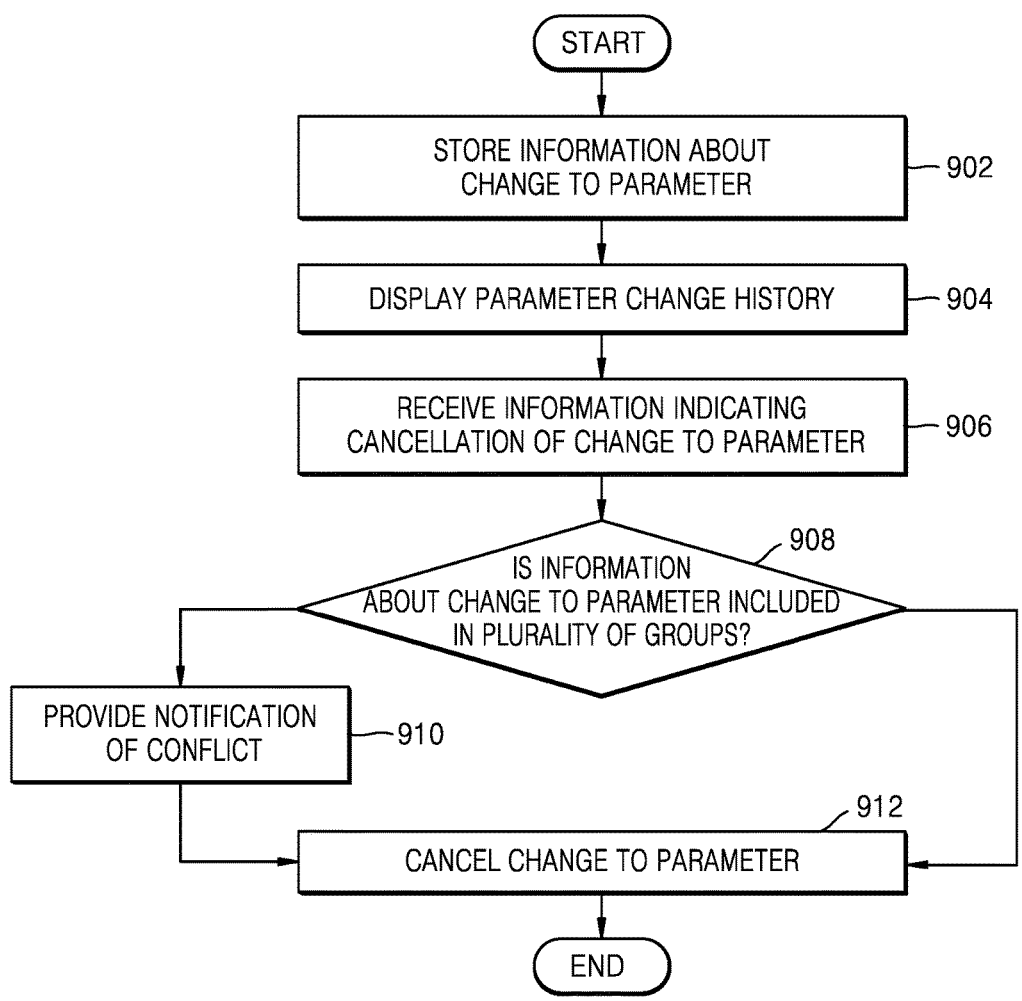
FIG. 9 is a flowchart of a method of cancelling editing of a parameter according to an exemplary embodiment.

FIG. 9 is a flowchart of a method of cancelling editing of a parameter according to an exemplary embodiment. The method of cancelling editing of parameters illustrated as a flowchart of FIG. 9 is another exemplary embodiment of the method of FIG. 4. Thus, although omitted hereinafter, the descriptions of the method of editing parameters with reference to FIG. 4 may also apply to the method of FIG. 9.

The parameter editing apparatus 100 stores, as one piece of group information, information about change to a parameter for capturing a medical image and an associated parameter which needs to be changed together with the parameter (operation 902).

The parameter editing apparatus 100 displays a parameter change history including at least one piece of group information (operation 904). Operations 902 and 904 may respectively correspond to operations 402 and 404.

The parameter editing apparatus 100 may receive, from a user, information indicating cancellation of a change to a first parameter included in the parameter change history (operation 906).

Figure 10:
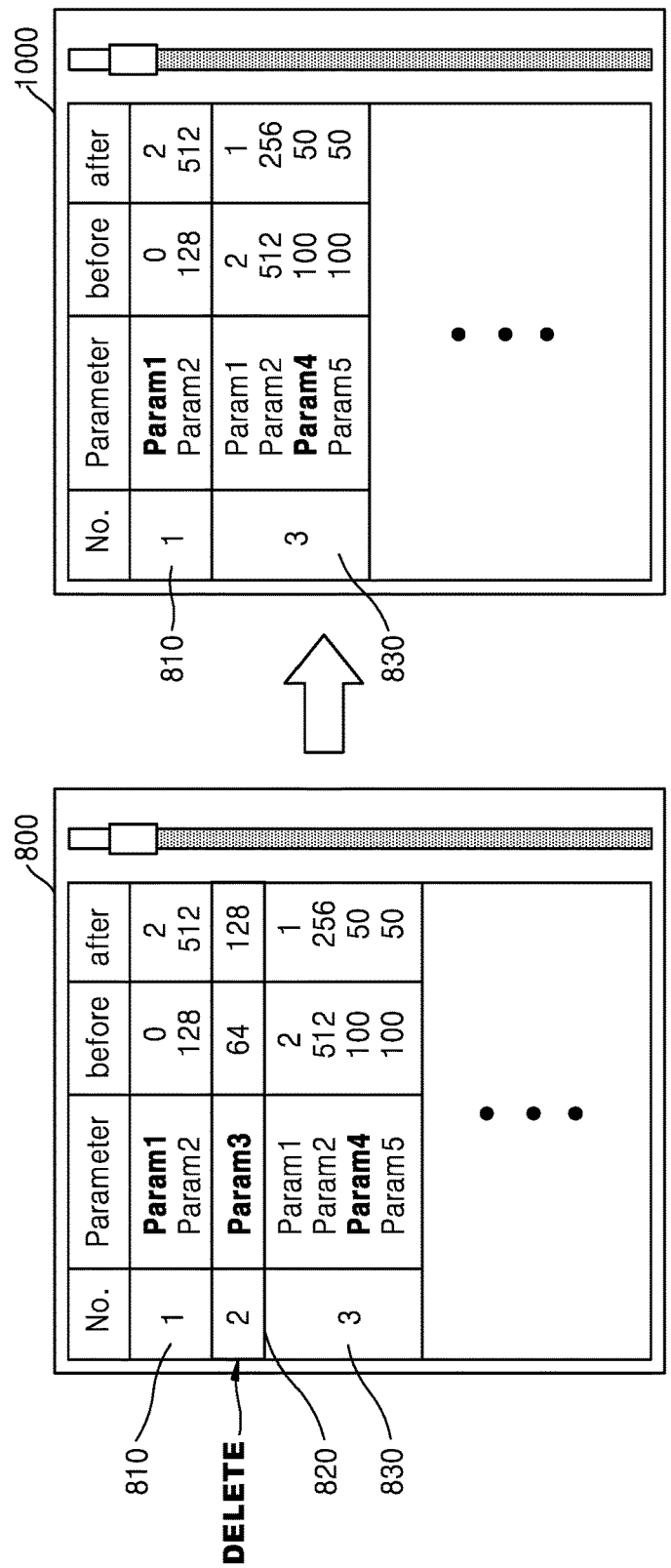
FIG. 10 illustrates an example of a method of editing a parameter editing history.

According to an exemplary embodiment, the parameter editing apparatus 100 may receive information indicating selection, by the user, of one from among groups included in the parameter editing history (e.g., 800 of FIG. 8). Referring to FIG. 10, the parameter editing apparatus 100 may receive information indicating selection, by the user, of group 2 820.

In an exemplary embodiment, the selected group may be displayed differently than other groups. For example, a background color or edge of the selected group may be displayed differently than those of the other groups.

The parameter editing apparatus 100 may receive information corresponding to a user input for deleting the selected group. Referring to FIG. 10, the parameter editing apparatus 100 may receive information indicating deletion of the selected group 2 820.

The parameter editing apparatus 100 may cancel a change to a first parameter included in the group 2 820 by deleting the group 2 820.

For example, the parameter editing apparatus 100 may cancel a change to a first parameter Param3 included in the group 2 820 by deleting the group 2 820. The parameter editing apparatus 100 may delete the group 2 820 as shown in a parameter change history 1000 after the deletion and change a value of the first parameter Param3 from '128', which is a value after the change, back to '64', which is the value before the change. After a change to a parameter due to deletion of a corresponding group, an additional group may not be created in the parameter change history.

According to another exemplary embodiment, the parameter editing apparatus 100 may delete group 3 830. In this case, changes to parameter Param4 changed based on a user input and all associated parameters Param1, Param2, and Param5 included in group 3 830 may all be cancelled.

Figure 11:
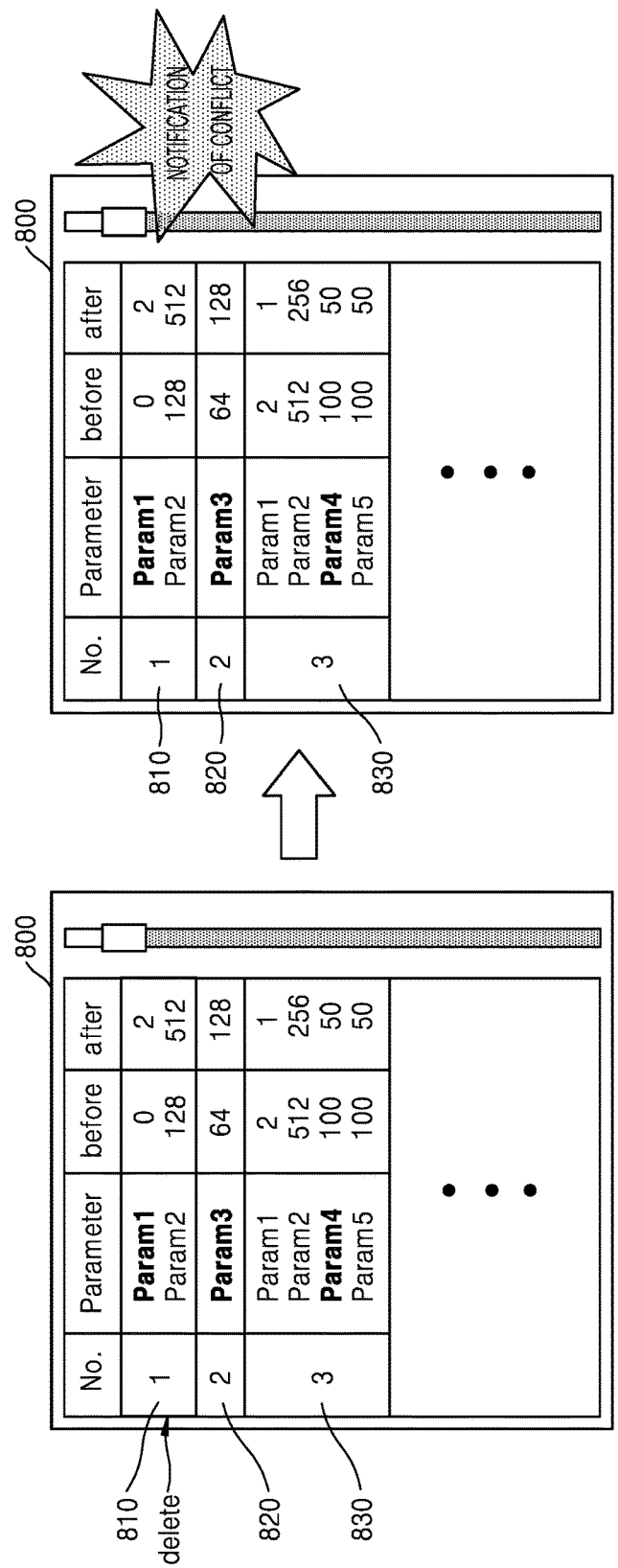
FIG. 11 illustrates an example of a method of providing a notification in a parameter editing history.

The parameter editing apparatus 100 may determine whether information about the change to the first parameter is included in a plurality of pieces of group information in the parameter change history (operation 908). In an exemplary embodiment, the parameter editing apparatus 100 may determine whether a conflict occurs between groups according to the information indicating cancellation, received in operation 906. For example, referring to FIG. 11, parameter Param3 is included in the group 2 820, but not in other groups, i. e., the group 1 810 and the group 3 830. Thus, deleting the group 2 820 does not cause a conflict to occur with the other groups 1 810 and group 3 830

In another exemplary embodiment, the parameter editing apparatus 100 may receive information indicating deletion of the group 1 801. However, because parameters Param1 and Param2 in the group 1 810 are also included in the group 3 830, deleting the group 1 810 may cause a conflict to occur with the group 3 830.

In an exemplary embodiment, the parameter editing apparatus 100 may determine that deleting the group 3 830 that is changed later than the group 1 810 does not cause a conflict with the group 1 810. In another exemplary embodiment, the parameter editing apparatus 100 may determine that deleting a group including the same parameter as that of another group causes a conflict with the other group regardless of the order in which the groups are changed.

When it is determined in operation 908 that a conflict does not occur, the parameter editing apparatus 100 may perform operation 912. The parameter editing apparatus 100 may cancel the change to the first parameter as shown in FIG. 10 (operation 912). On the other hand, when it is determined in operation 908 that a conflict occurs, the parameter editing apparatus 100 may perform operation 910.

Figure 12:
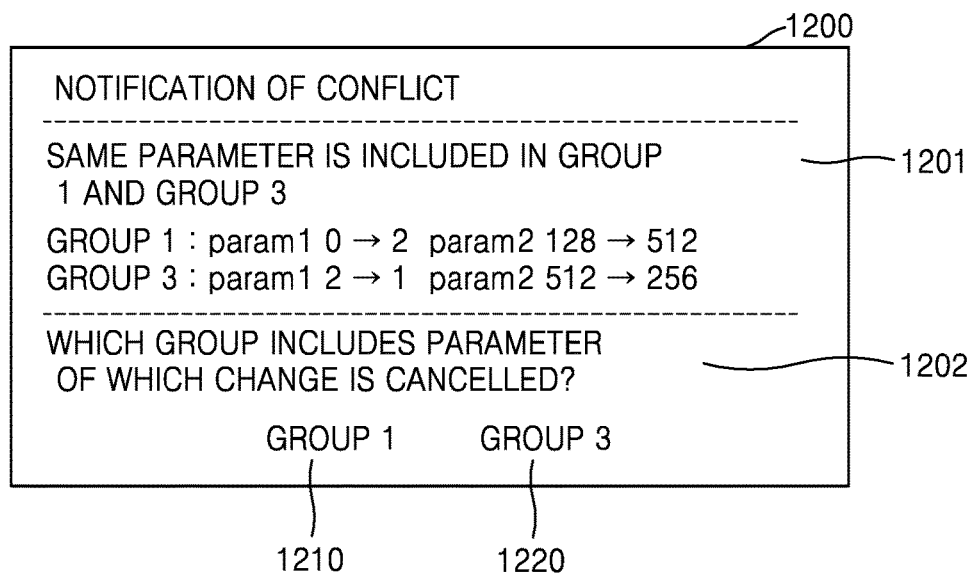
FIG. 12 illustrates an example of displaying a conflict notification according to an exemplary embodiment.

The parameter editing apparatus 100 may provide the user with a notification indicating that the conflict has occurred (operation 910). According to an exemplary embodiment, the parameter editing apparatus 100 may provide a notification via the display 103. Referring to FIG. 12, the parameter editing apparatus 100 may provide the user with a notification indicating the conflict has occurred by using a pop-up window 1200.

A field 1201 in the pop-up window 1200 may indicate detailed information about a conflict. For example, the field 1201 may indicate groups and parameters in which the conflict occurs. In an exemplary embodiment, the pop-up window 1200 may include a field 1202 requesting selection from the user. The parameter editing apparatus 100 may accurately identify a group which the user intends to delete by using the field 1202.

For example, the parameter editing apparatus 100 may check which of group 1 and group 3 is intended to be deleted by the user by using the field 1202. By checking the group intended for deletion, the parameter editing apparatus 100 may prevent a change to a parameter that is not actually intended by the user.

When the conflict has been resolved in operation 910, the parameter editing apparatus 100 may perform operation 912.

For example, if the user selects a 'group 3' button 1220, a value of parameter Param1 may be changed to '2' that is a value of before field for the group 3. Furthermore, a value of parameter Param2 may be changed to '512' that is a value of before field for the group 3.

As another example, if the user selects a 'group 1' button 1210, a value of parameter Param1 may be changed to '0' that is a value of before field for the group 1. Furthermore, a value of parameter Param2 may be changed to '128' that is a value of before field for the group 1.

According to an exemplary embodiment, if cancellation of a change to a parameter in the group 1 is allowed as described above, a parameter change history of the remaining group 3 may not match current parameter values. In this case, the parameter editing apparatus 100 may create a new group due to the change to the parameter in the group 1 and add the created new group to the parameter change history 800.

For example, the parameter editing apparatus 100 may create group 4. The group 4 may include a change of parameter Param1 from '1' to '0' and a change of parameter Param2 from '256' to '128'. According to another exemplary embodiment, in order to avoid such inconsistency, the parameter editing apparatus 100 may not allow cancellation of a change to a parameter in the group 1 which has been changed first.

Figure 13:
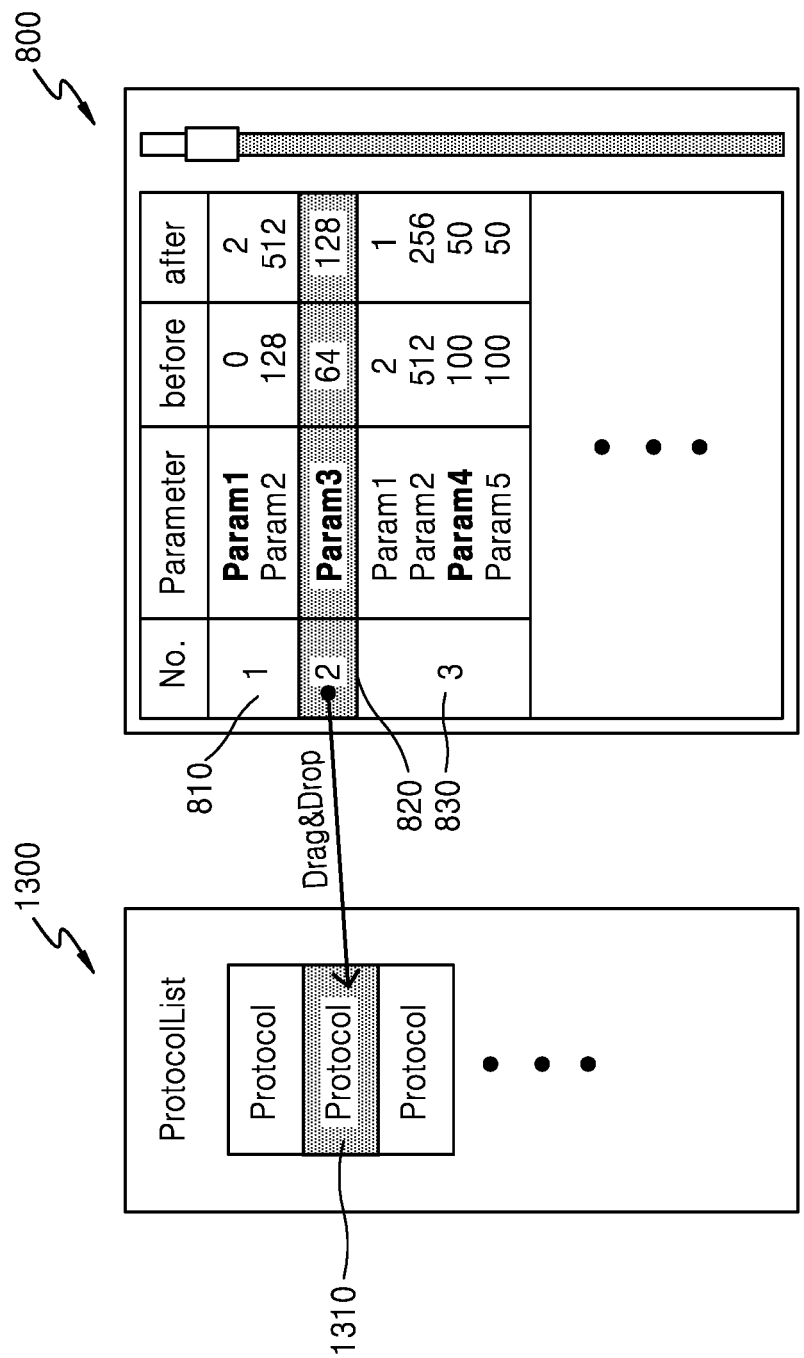
FIG. 13 illustrates an example of a method of applying a parameter change history for a current protocol to another protocol.

FIG. 13 illustrates an example of a method of applying a parameter change history for a current protocol to another protocol. In the present specification, a protocol may be one imaging session. For example, according to a position or object to be scanned, a scan may be performed by applying different parameters within a single imaging process. Thus, a single imaging process may be separated into several protocols that are imaging sessions to be sequentially performed.

In the specification, a change to a parameter and a parameter change history may be applied within one protocol. According to an exemplary embodiment, a parameter change history for a current protocol may need to be applied to another protocol. In this case, the parameter editing apparatus 100 may receive a user input for selecting at least one group from among groups 810, 820, and 830 included in the parameter change history 800. Furthermore, the parameter editing apparatus 100 may receive a user input for selecting one protocol 1310 from among protocols in a protocol list 1300. In this case, the parameter editing apparatus 100 may apply a parameter change history corresponding to the selected group to the selected protocol 1310 as well.

In an exemplary embodiment, the parameter editing apparatus 100 may receive information about a drag & drop operation performed by dragging and dropping the selected group 2 820 onto the selected protocol 1310. In this case, the parameter editing apparatus 100 may change a value of parameter Param3 in the group 2 820 for the selected protocol 1310 to '128' that is a value of parameter Param3 in the group 2 820.

The exemplary embodiments can be written as computer programs and can be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs or DVDs), etc.

While exemplary embodiments have been particularly shown and described, it will be understood by those of ordinary skill in the art that various changes in form and details may be made therein without departing from the spirit and scope as defined by the following claims.

What is claimed is:

1. An apparatus for editing information about a parameter for capturing a medical image, the apparatus comprising:
   a storage device configured to store at least one piece of group information including information about a change to the parameter for capturing the medical image and an associated parameter to be changed together with the parameter;
   a display configured to display a parameter change history including the at least one piece of group information; and
   a processor configured to control the display and the storage device; and
   a user input device configured to receive, from a user, a selection of first group information from the at least one piece of group information, the first group information being included in the parameter change history, and to receive information indicating deletion of the first group information,
   wherein the at least one piece of group information is arranged based on an order in which a parameter in the at least one piece of group information is changed, and
   wherein the processor is further configured to:
      define parameters included in the first group information which are also included in second group information included in the parameter change history, and
      selectively cancel a change to parameters in the first group information based on the defined parameters and deletion of the first group information.

2. The apparatus of claim 1, the user input device being further configured to receive, from a user, information about a change to the parameter,
   wherein the processor is further configured to change the parameter based on the received information, to change, if the parameter has an associated parameter to be changed together with the parameter, the associated parameter, and to control the storage device to store information about the change to the parameter and the change of the associated parameter as the at least one piece of group information.

3. The apparatus of claim 2, wherein the display is further configured to display the changed parameter in such a manner as to distinguish the changed parameter from the associated parameter.

4. The apparatus of claim 2, wherein the user input device is further configured to receive, from the user, a selection of the at least one piece of group information in the parameter change history and a selection of an imaging protocol, and
   wherein the processor is further configured to change, based on information about a change to a parameter in the at least one piece of group information, a corresponding parameter for the imaging protocol.

5. The apparatus of claim 1, wherein the display is further configured to display the parameter and the associated parameter in such a manner as to distinguish the parameter from the associated parameter.

6. The apparatus of claim 1, wherein the processor is further configured to control the display to display a notification when information about a change to a parameter included in the first group information is included in a plurality of pieces of group information in the parameter change history.

7. The apparatus of claim 6, wherein the user input device is further configured to receive a selection of one piece of group information from among the plurality of pieces of group information, and
   wherein the processor is further configured to cancel a change to a parameter included in the one piece of group information.

8. The apparatus of claim 1, wherein the parameter relates to at least one condition used by the apparatus when performing at least one from among emitting radiation toward an object, detecting radiation that has passed through the object, and reconstructing an image using the detected radiation.

9. The apparatus of claim 1, wherein the associated parameter relates to at least one condition used by the apparatus when performing at least one from among emitting radiation toward an object, detecting radiation that has passed through the object, and reconstructing an image using the detected radiation.

10. A method of editing information about a parameter for capturing a medical image, the method comprising:
    storing at least one piece of group information including information about a change to the parameter for capturing a medical image and an associated parameter to be changed together with the parameter;
    displaying a parameter change history including the at least one piece of group information;
    receiving, from a user, a selection of first group information from the at least one piece of group information, the first group information being included in the parameter change history;
    receiving, from the user, information indicating deletion of the first group information;
    defining parameters included in the first group information which are also included in second group information included in the parameter change history; and
    canceling a change to parameters in the first group information based on the defined parameters and deletion of the first group information,
    wherein the at least one piece of group information is arranged based on an order in which a parameter in the at least one piece of group information is changed.

11. The method of claim 10, wherein the storing of the information about the change to the parameter comprises:
    receiving, from a user, the information about the change to the parameter;
    changing the parameter based on the received information; and
    changing, if the parameter has an associated parameter to be changed together with the parameter, the associated parameter.

12. The method of claim 11, wherein the changing of the parameter based on the received information comprises displaying the changed parameter in such a manner as to distinguish the changed parameter from the associated parameter.

13. The method of claim 11, further comprising:
    receiving, from the user, a selection of the at least one piece of group information in the parameter change history;
    receiving a selection of an imaging protocol from the user; and
    changing, based on information about a change to a parameter in the at least one piece of group information, a corresponding parameter for the imaging protocol.

14. The method of claim 10, wherein the displaying of the parameter change history comprises displaying the parameter and the associated parameter in such a manner as to distinguish the parameter from the associated parameter.

15. The method of claim 10, wherein the canceling a change to parameters in the first group information based on the defined parameters and the deletion of the first group information further comprises displaying a notification when information about a change to a parameter in the first group information is included in the second group information in the parameter change history.

16. The method of claim 15, wherein the displaying of the notification comprises:
   receiving, from the user, information indicating selection of one piece of group information from among the second group information; and
   cancelling a change to a parameter included in the one piece of group information.

17. A non-transitory computer-readable recording medium having recorded thereon a program which, when executed, causes a processor to perform the method of claim 10.

* * * * *